United States Patent [19]  [11]  4,401,819
Cordier et al.  [45]  Aug. 30, 1983

[54] PROCESS FOR THE PREPARATION OF PYRIDINE AND SUBSTITUTED PYRIDINES

[75] Inventors: Georges Cordier, Francheville; Patrick Leroux, Meudon, both of France

[73] Assignee: Rhone-Poulenc Specialites Chimiques, Courbevoie, France

[21] Appl. No.: 360,567

[22] Filed: Mar. 22, 1982

[30] Foreign Application Priority Data

Apr. 1, 1981 [FR] France ............................... 81 06692

[51] Int. Cl.³ ................ C07D 213/133; C07D 213/09
[52] U.S. Cl. ..................................... 546/252; 546/251
[58] Field of Search ................................ 546/251, 252

[56] References Cited

U.S. PATENT DOCUMENTS

| 2,765,310 | 10/1956 | Horrobin | 546/252 |
| 2,765,311 | 10/1956 | Horrobin et al. | 546/252 |
| 4,086,237 | 4/1978 | Daum et al. | 546/252 |
| 4,332,943 | 6/1982 | Bleker et al. | 546/253 |

FOREIGN PATENT DOCUMENTS

| 46897 | 11/1981 | European Pat. Off. | 542/252 |
| 1192648 | 11/1955 | Fed. Rep. of Germany | 546/252 |
| 1102356 | 5/1955 | France | 546/252 |
| 2309535 | 11/1976 | France | 546/252 |
| 2356638 | 1/1978 | France | 546/252 |
| 745400 | 2/1956 | United Kingdom | 546/252 |
| 1011322 | 11/1965 | United Kingdom | 546/252 |
| 1393086 | 5/1975 | United Kingdom | 546/252 |
| 1494885 | 12/1977 | United Kingdom | 546/252 |
| 1583187 | 1/1981 | United Kingdom | 546/252 |

Primary Examiner—Robert T. Bond
Attorney, Agent, or Firm—Burns, Doane, Swecker & Mathis

[57] ABSTRACT

The present invention relates to a process for the preparation of pyridine and substituted pyridines, in the vapor phase. These compounds are obtained by heating, at a temperature of 200° to 500° C., in the vapor phase: piperidine or piperidine substituted by one or more lower alkyl radicals;

1,5-diaminopentane;

1,5-diaminopentane containing, in its hydrocarbon part, from 1 to 3 linear or branched alkyl radicals having from 1 to 4 carbon atoms; or compounds such as: N,N'-bis-(piperidin-2-yl)hydrazines, in the presence of a catalyst consisting of palladium, platinum or ruthenium deposited on a macroporous solid.

The products obtained by the process according to the invention have various uses. Pyridine is used in particular as a solvent. β-Picoline (or 3-methylpyridine) is used for the preparation of nicotinic acid or nicotinamide, used in pharmacy and in nutrition.

20 Claims, No Drawings

PROCESS FOR THE PREPARATION OF PYRIDINE AND SUBSTITUTED PYRIDINES

The present invention relates to a process for the preparation of pyridine and substituted pyridines, in the vapor phase, from optionally substituted piperidine, optionally substituted 1,5-diaminopentane, higher molecular products, such as N,N'-bis-(piperidin-2-yl)hydrazines optionally containing substituents on the piperidine rings, or mixtures of several of these compounds.

Processes for the preparation of pyridine by the catalytic dehydrogenation of piperidine, in the vapor phase, have already been disclosed in the prior art.

Thus, French Pat. No. 1,102,356 describes a process for the catalytic dehydrogenation of piperidine to pyridine by passing piperidine vapors and hydrogen over a platinum or palladium catalyst deposited on a silica gel, at a temperature of 200° to 500° C.

The silica gel used as a support is not defined by its characteristics such as the pore diameter or the porous volume; now, experiments show that not all the supports are equivalent for obtaining good results.

Examined German Application No. 1,192,648 also describes a process for the preparation of pyridine by the catalytic dehydrogenation of piperidine, in the vapor phase, on a catalyst based on platinum or palladium deposited on a silica gel, at a temperature situated between 200° and 400° C.

The productivity seems to be low for this process, according to the values indicated in the examples.

Finally, French Pat. No. 76/12,627 (published under No. 2,309,535) describes a process for the preparation of 3-methylpyridine from 2-methyl-1,5-diaminopentane and 3-methylpiperidine, at a temperature between 200° and 400° C., in the presence of palladium, platinum or nickel deposited on alumina, kieselguhr or pumice or on similar supports. The productivity in terms of 3-methylpyridine per hour and per liter of catalyst drops sharply after a few hours of operation and reaches low values, making the process of little economic value.

A process with excellent productivity has now been found for the preparation of pyridine and substituted pyridines, in the vapor phase, by the cyclization and/or dehydrogenation of optionally substituted 1,5-diaminopentane, optionally substituted piperidine, or other compounds such as N,N'-bis-(piperidin-2-yl)hydrazines, using a catalyst consisting of palladium, platinum or ruthenium deposited on a macroporous solid support; it is this process which forms a subject of the present invention.

More precisely, the process according to the invention is a process for the preparation of compounds of the general formula (I):

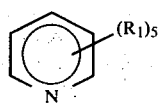

in which the radicals $R_1$, which are identical or different, represent a hydrogen atom or a linear or branched alkyl radical having 1 to 4 carbon atoms, by heating, in the vapor phase:

a compound of the general formula (II):

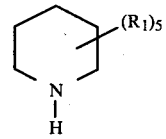

in which the radicals $R_1$ have the same meanings as above, or 1,5-diaminopentane, or 1,5-diaminopentane containing, in its hydrocarbon part, from 1 to 3 linear or branched alkyl radicals having from 1 to 4 carbon atoms, or a compound of the general formula (III):

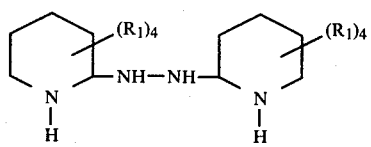

in which the radicals $R_1$ have the meanings indicated above, or a mixture of several of the above compounds, the said process being characterized in that the reaction is carried out in the presence of a catalyst consisting of palladium, platinum or ruthenium deposited on a macroporous solid support of which the average pore diameter is more than 200 Angstroms and of which the porous volume is between 0.5 and 1.4 cubic centimeters/gram.

It is preferred to use a macroporous support of which the average pore diameter is between 300 Angstroms and 5,000 Angstroms and of which the porous volume is between 0.8 and 1.2 cm$^3$/g.

The macroporous solid support can be any solid normally used as a catalyst support, provided that its average pore diameter has one of the values indicated above.

Thus, alumina, carbon or silica, for example, can be used as the support.

Silica is very particularly suitable because microbeads of silica having the desired characteristics indicated above can be prepared at will. The preferred silicas have an average pore diameter of between 300 A and 2,000 A and a porous volume of between 0.8 and 1.2 cm$^3$/g.

For the preparation of such silicas, reference may be made, in particular, to the technique described in French Pat. No. 70/20,514 (publication No. 2,093,176), which relates to a treatment of dried silicious hydrogels in an autoclave, in an ammoniacal reaction medium.

The contents of the said patent are incorporated in the present description by way of reference.

The particle size of the support used for the preparation of the catalyst is not a critical parameter. It depends essentially on the dimensions of the reactor.

The techniques of deposition of the metal on the macroporous support are well known to those skilled in the art.

Amongst the abovementioned metals, it is generally preferred to use palladium deposited on silica, on alumina or on carbon. Palladium deposited on the silicas described above is very particularly suitable as a catalyst in the process according to the invention.

If it is desired to prepare a Pd-on-silica catalyst, it is possible, for example, to carry out impregnation by exchange, using ammoniacal solutions of tetramminopalladium chloride, in the presence of ammonium chloride.

The weight ratio metal/macroporous solid support is generally less than or equal to 10%. This ratio is most frequently between 0.1% and 5%. It is preferably situated between 0.2% and 2% for Pd-on-silica catalysts.

As a general rule, if the supports used have an average pore diameter which tends towards the lowest values indicated, it is favorable to use weight ratios metal/-support which are situated in the lower part of the ranges indicated above.

The amount of catalyst, relative to the compound to be cyclized and/or dehydrogenated (or substrate) used, is not critical. However, as it is most common to use a catalyst bed in which the substrate circulates in the vapor state, the amount and the layer of catalyst must be sufficient to ensure the desired degree of conversion, taking account of the contact time between the substrate vapors and the catalyst.

The temperature at which the process according to the invention is carried out must be sufficient for the starting reactants to be in the vapor state and for the reaction to be sufficiently rapid. It has been found that temperatures of 200° to 500° C. are suitable. The reaction is preferably carried out at temperatures between 250° C. and 400° C.

When the process according to the invention is carried out, it is generally favorable to inject hydrogen into the reactor in which the cyclization reaction and/or dehydrogenation reaction is to take place, simultaneously with the injection of the substrate to be treated. The molar ratio hydrogen/substrate is not critical and can vary within very wide limits. For example, it can be between 0.1 and 500. However, hardly any advantage is gained by adopting an excessively high ratio, which reduces the partial pressure of the substrate and decreases its residence time in the reactor.

Usually, molar ratios hydrogen/substrate of 0.5 to 10 are suitable.

The compounds to which the process according to the invention can be applied in particular are:
piperidine;
piperidine of which the ring is substituted by one or more methyl or ethyl radicals;
1,5-diaminopentane;
1,5-diaminopentane of which the hydrocarbon part contains one or more methyl or ethyl substituents;
N,N'-bis-(piperidin-2-yl)-hydrazine;
N,N'-bis-(piperidin-2-yl)-hydrazine of which one piperidinyl ring or both the piperidinyl rings carry one or more methyl or ethyl radicals; and
mixtures of several of the above compounds.

Amongst these compounds, the process according to the invention is very particularly suitable for:
piperidine;
piperidine of which the ring is substituted by one or two methyl or ethyl radicals, such as, for example: 3-methylpiperidine, 2-methylpiperidine, 4-methylpiperidine, 2-ethylpiperidine, 3-ethylpiperidine, 4-ethylpiperidine, 2,3-dimethylpiperidine, 2,4-dimethylpiperidine, 2,5-dimethylpiperidine, 3,4-dimethylpiperidine, 3,5-dimethylpiperidine, 2,3-diethylpiperidine, 2,4-diethylpiperidine, 2,5-diethylpiperidine, 3,4-diethylpiperidine, 3,5-diethylpiperidine, 2-ethyl-3-methylpiperidine, 3-ethyl-2-methylpiperidine, 2-ethyl-4-methylpiperidine, 4-ethyl-2-methylpiperidine, 2-ethyl-5-methylpiperidine, 5-ethyl-2-methylpiperidine, 3-ethyl-4-methylpiperidine, 4-ethyl-3-methylpiperidine, 3-ethyl-5-methylpiperidine and 5-ethyl-3-methylpiperidine;
1,5-diaminopentane;
1,5-diaminopentanes of which the hydrocarbon part contains one or 2 methyl or ethyl substituents, such as, for example: 1-methyl-1,5-diaminopentane, 2-methyl-1,5-diaminopentane, 3-methyl-1,5-diaminopentane, 1-ethyl-1,5-diaminopentane, 2-ethyl-1,5-diaminopentane, 3-ethyl-1,5-diaminopentane, 1,2-dimethyl-1,5-diaminopentane, 1,3-dimethyl-1,5-diaminopentane, 1,4-dimethyl-1,5-diaminopentane, 2,3-dimethyl-1,5-diaminopentane and 2,4-dimethyl-1,5-diaminopentane;
N,N'-bis-(piperidin-2-yl)-hydrazine; and
N,N'-bis-(piperidin-2-yl)-hydrazine of which one piperidinyl ring or both the piperidinyl rings carry one or two methyl or ethyl radicals, such as, for example: N,N'-bis-(3-methylpiperidin-2-yl)-hydrazine, N-(3-methylpiperidin-2-yl)-N'-(5-methylpiperidin-2-yl)-hydrazine, N,N'-bis-(5-methylpiperidin-2-yl)-hydrazine, N,N'-bis-(3-ethylpiperidin-2-yl)-hydrazine and N,N'-bis-(5-ethylpiperidin-2-yl)-hydrazine.

It is of course possible to use mixtures of several of the above compounds, in particular mixtures which, on cyclization and/or dehydrogenation, lead to the same final compound of the formula (I).

The catalyst used in the process according to the invention is very advantageous because it makes it possible to obtain pyridine or pyridines substituted by methyl and/or ethyl radicals from piperidine, 1,5-diaminopentane or their methyl-substituted and/or ethyl-substituted derivatives, or from so-called high molecular compounds originating from the condensation of intermediates obtained during the hydrogenation of glutaronitrile or of glutaronitrile substituted by methyl and/or ethyl radicals.

Thus, it is possible, in particular, to apply the process according to the invention to the mixture of compounds obtained during the hydrogenation of 2-methylglutaronitrile, without it being necessary to isolate its various constituents. This also makes it possible to utilize the products formed by the condensation of intermediates.

Thus, if 2-methylglutaronitrile is hydrogenated on Raney nickel, this essentially gives a mixture of 2-methyl-1,5-diaminopentane, 3-methylpiperidine, N,N'-bis-(3-methylpiperidin-2-yl)-hydrazine, N,N'-bis-(5-methylpiperidin-2-yl)-hydrazine and N-(3-methylpiperidin-2-yl)-N'-(5-methylpiperidin-2-yl)-hydrazine, which can be treated directly by the process according to the invention.

The process according to the invention is therefore preferably applied to these hydrogenation products of 2-methylglutaronitrile, to the hydrogenation products of glutaronitrile, such as 1,5-diaminopentane, piperidine and N,N'-bis-(piperidin-2-yl)-hydrazine, to 5-ethyl-2-methylpiperidine and to mixtures of several of these compounds, which finally leads either to $\beta$-picoline, or to pyridine, or to 5-ethyl-2-methylpyridine, or to mixtures of pyridine and its derivatives.

The equipment used for carrying out the process according to the invention is not specific. Any equipment which makes it possible to operate in the vapor phase can be used.

From a practical point of view, it is possible, for example, to carry out the process according to the invention using the following procedure. The catalyst is deposited in a suitable reactor as a layer, the thickness of which is determined as a function of the flow rate of substrate to be treated. This layer of catalyst can also be arranged either under a layer of an inert solid, such as quartz, having a particle size of the same order of magnitude as that of the catalyst, or between two layers of an inert solid of this type; the layer of catalyst can also be mixed with an inert solid of this type.

The layer of catalyst and the possible layers of inert solid are heated to the desired temperature.

The substrate to be treated and the hydrogen are injected simultaneously into an enclosure heated to a sufficient temperature to vaporize the said substrate.

The reaction products are then condensed into a low-temperature enclosure, if appropriate containing a solvent for these products.

The final reaction mixture is treated in accordance with the conventional chemical methods, and the determinations of its various compounds are carried out, for example, by vapor phase chromatography.

The catalyst of the process according to the invention retains a good activity, even after several hundred hours of use. However, if it is considered necessary, it can be reactivated, for example by heating it to a temperature above that at which it was used.

The products obtained by the process according to the invention have various uses. Pyridine is used in particular as a solvent. $\beta$-Picoline (or 3-methylpyridine) is used for the preparation of nicotinic acid or nicotinamide, used in pharmacy and in nutrition. 5-Ethyl-2-methylpyridine is also used as an intermediate for the preparation of nicotinic acid. The examples which follow are given to illustrate the invention. In order to give a better definition of the performance characteristics of the catalysts used in the process according to the invention, and in particular in order to compare their activity and their life with those of catalysts not possessing their characteristics, in particular the catalysts used in the processes of the prior art, the productivity of the catalyst was determined in the examples which follow, in addition to the degree of conversion of the substrates used and the yield of compound of the formula (I) obtained. This productivity is expressed in grams of compound of the formula (I) obtained per hour and per liter of catalyst used.

EXAMPLE 1

The following are arranged successively, from bottom to top, in a vertically placed glass microreactor having a height of 200 mm and a diameter of 15 mm;

a first, 65 mm thick layer of inert quartz having a particle size of between 250 microns and 315 microns (volume of the layer: 10 cm$^3$);

a layer of catalyst consisting of 0.6% by weight of palladium deposited on microbeads of silica (particle size of 150 to 300 microns) having a porous volume of 0.94 cm$^3$ per gram, having an average pore diameter of about 500 Angstroms and having a specific surface area of 67 m$^2$/gram (Volume of the layer: 1 cm$^3$); and a second layer of quartz, identical to the first.

The microreactor is fitted with a central thermometer pocket, a set of thermocouples at different levels of the catalyst bed, in order to monitor its temperature, an electrical heating system and a system of injection by syringe-type micropump at its upper end.

In the lower part of the microreactor, there is a receiver containing ethanol kept at −15° C., in which the reaction products are to be condensed.

The temperature of the catalyst layer is regulated at 270° C. Through the top of the reactor, hydrogen, with a flow rate of 1.3 liters/hour (volume calculated for normal temperature and pressure conditions: NTP), and 3-methylpiperidine, with an exactly measured flow rate of about 2.0 grams/hour, are injected conjointly into the injection chamber which constitutes the top part of the reactor and which is at 150° C. The 3-methylpiperidine is instantaneously vaporized in this injection chamber. The reaction products are condensed and collected in the ethanol, and the solution obtained is analyzed by vapor phase chromatography.

The degree of conversion (DC) of the 3-methylpiperidine, the yield (Y) of $\beta$-picoline (3-methylpyridine) obtained, relative to the 3-methylpiperidine converted, and the productivity in grams of $\beta$-picoline per hour and per liter of catalyst, are calculated.

Table 1 below collates the instantaneous values of the DC and the Y and also the productivity calculated for various operating times.

TABLE 1

| Time in hours | DC % of the 3-methylpiperidine | Y % of $\beta$-picoline | Productivity in terms of $\beta$-picoline (in g/hour/liter) |
| --- | --- | --- | --- |
| 1 | 98 | 100 | 2,000 |
| 20 | 75 | 100 | 1,400 |
| 80 | 48 | 100 | 920 |
| 240 | 30 | 100 | 550 |
| 320 | 30 | 100 | 550 |

The temperature of the catalyst layer is then raised to about 330° C. (injection chamber: 210° C.).

The hydrogen flow rate is maintained at its previous value and the flow rate of the 3-methylpiperidine is increased to an exactly measured value of about 5.5 g/hour. Table 2 below collates the values of the DC, the Y and the productivity for various reaction times at about 330° C. (the total duration of the experiment, that is to say the 320 hours of operation at 270° C. together with the hours of operation at about 330° C., is indicated in brackets).

TABLE 2

| Time in hours | DC % | Y % of $\beta$-picoline | Productivity in terms of $\beta$-picoline (in g/hour/liter) |
| --- | --- | --- | --- |
| 1 (321) | 60 | 100 | 3,300 |
| 40 (360) | 65 | 100 | 3,580 |
| 100 (420) | 67 | 100 | 3,630 |

The degree of conversion is deliberately kept below 100% in order to find out the maximum productivity at a given instant and thus be able to record any possible decreases in this productivity.

EXAMPLE 2

The same equipment and the same procedure are used as in Example 1.

The catalyst layer is made up as in Example 1, with the same batch of catalyst, but it is kept at 300° C. (injection chamber: 180° C.).

The hydrogen flow rate is 3.7 liters/hour (NTP) and the flow rate of the 3-methylpiperidine injected is 5.0 g/hour. The duration of the experiment is 1 hour. The following results are obtained:

| | | |
| --- | --- | --- |
| DC of the 3-methylpiperidine | = | 98% |
| Y of $\beta$-picoline | = | 99% |

| Productivity in terms of β-picoline | = | 4,560 g/hour per liter of catalyst |
|---|---|---|

EXAMPLE 3

The same equipment and the same procedure as in Example 1 are used.

The catalyst layer is made up as in Example 1, with the same batch of catalyst, but it is kept at 350° C. (injection chamber: 230° C.).

The hydrogen flow rate is 3.7 liters/hour (NTP) and the flow rate of the 3-methylpiperidine injected is 12.0 g/hour. The duration of the experiment is 1 hour. The following results are obtained:

| DC of the 3-methylpiperidine | = | 96% |
|---|---|---|
| Y of β-picoline | = | 99% |
| Productivity in terms of β-picoline | = | 10,700 g/hour per liter of catalyst |

EXAMPLE 4

The same equipment and the same procedure as in Example 1 are used.

The catalyst layer is made up as in Example 1, with the same batch of catalyst, but it is kept at 300° C. (injection chamber: 180° C.).

The hydrogen flow rate is 3.7 liters/hour (NTP) and 2-methyl-1,5-diaminopentane is injected conjointly with a flow rate of 1.4 g/hour. The duration of the experiment is 1 hour. The following results are obtained:

| DC of the 2-methyl-1,5-diaminopentane | = | 100% |
|---|---|---|
| Y of β-picoline | = | 75% |
| Y of 3-methylpiperidine | = | 25% |

EXAMPLE 5

The same equipment and the same procedure as in Example 1 are used.

The catalyst layer is made up as in Example 1, with the same batch of catalyst, but it is kept at 350° C. (injection chamber: 230° C.).

The hydrogen flow rate is 3.7 liters/hour (NTP) and "high molecular" compounds originating from the hydrogenation of 2-methylglutaronitrile and having the general formula:

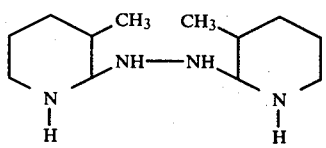

are injected conjointly with a flow rate of 4.0 g/hour. The duration of the experiment is 1 hour.
The following results are obtained:

| DC of the said "high molecular" compounds | = | 100% |
|---|---|---|
| Y of β-picoline | = | 85% |
| Y of 3-methylpiperidine | = | 3% |

EXAMPLE 6

Example 5 is repeated, a crude mixture originating from the hydrogenation of 2-methylglutaronitrile being injected with an exactly measured flow rate of about 1.3 g/hour, in the presence of ammonia, on Raney nickel, under a total pressure ($NH_3$+hydrogen) of 50 bars and then of 75 bars, and at a temperature of 80° C. and then of 100° C.; this mixture has the following composition:

| 3-methylpiperidine: | 59% by weight |
|---|---|
| 2-methyl-1,5-diaminopentane: | 31.7% by weight |
| "high molecular" compounds such as those treated in Example 5: | 9.3% by weight. |

Table 3 collates the compositions of the final reaction mixture (in % by weight) after various operating times, and the productivity obtained in terms of β-picoline.

TABLE 3

| Time in hours | % of β-picoline | % of 3-methyl-piperidine | % of 2-methyl-1,5-diamino-pentane | % of "high molecular" compounds | Productivity in terms of β-picoline g/hour/liter of catalyst |
|---|---|---|---|---|---|
| 95 | 82.7 | 10.5 | 3.9 | 2.9 | 760 |
| 261 | 44.7 | 41.3 | 10.8 | 3.2 | 480 |
| 457 | 65.3 | 23.8 | 8.0 | 2.9 | 625 |

COMPARISON EXPERIMENTS

These experiments are carried out under the same conditions as the previous examples, but by using either commercial catalysts or a catalyst of which the support does not correspond to the macroporosity characteristics of the catalysts of the process according to the invention.

EXPERIMENT A

The same equipment and the same procedure as in Example 1 are used.

The catalyst layer is made up as in Example 1, but by using, as the catalyst, palladium deposited in a proportion of 0.5% on an alumina having a particle size of 250 to 315 microns, a porous volume of 0.30 cm³/g, an average pore diameter of 28 A and a specific surface area of 220 m²/g.

The catalyst layer is kept at 300° C. (injection chamber: 180° C.).

The hydrogen flow rate is 3.7 liters/hour (NTP) and 3-methylpiperidine is injected conjointly with a flow rate of 0.33 g/hour.

Table 4 collates the values of the DC, the Y and the productivity for various operating times.

TABLE 4

| Time in hours | DC % of the 3-methylpiperidine | Y % of β-picoline | Producivity in terms of β-picoline (g/hour/liter) |
|---|---|---|---|
| 1 | 95 | 100 | 295 |
| 3 | 55 | 100 | 170 |
| 20 | 25 | 100 | 77 |

TABLE 4-continued

| Time in hours | DC % of the 3-methylpiperidine | Y % of β-picoline | Productivity in terms of β-picoline (g/hour/liter) |
|---|---|---|---|
| 30 | 10 | 100 | 30 |

It is noted that the productivity values are lower than with the catalyst used in Examples 1 to 6, and that this catalyst is rapidly deactivated, which results in a corresponding decrease in the said productivity.

EXPERIMENT B

Experiment A is repeated, but the Pd-on-Al$_2$O$_3$ is replaced by a catalyst sold by ENGELHARD, which is Pd deposited in a proportion of 0.5% by weight on silica, having a porous volume of 1.04 cm$^3$/g, an average pore diameter of 100 A and a specific surface area of 293 m$^2$/g.

The temperature of the catalyst layer is 300° C. (injection chamber: 180° C.).

The hydrogen flow rate is 3.7 liters/hour (NTP) and 1.7 g/hour of 3-methylpiperidine are injected conjointly.

Table 5 collates the values of the DC, the Y and the productivity for various operating times.

TABLE 5

| Time in hours | DC % of the 3-methylpiperidine | Y % of β-picoline | Productivity in terms of β-picoline (g/hour/liter) |
|---|---|---|---|
| 7 | 14.1 | 100 | 105 |
| 23 | 11 | 100 | 81 |
| 46 | 7.4 | 100 | 94 |
| 63 | 3.2 | 100 | 63 |

In this experiment, a low initial productivity, which decreases very rapidly, is again observed.

EXPERIMENT C

The same equipment and the same procedure as in Example 1 are used.

The catalyst layer is made up as in Example 1, but by using, as the catalyst, palladium deposited in a proportion of 1.6% on a silica having a particle size of 150 to 300 microns, a porous volume of 0.91 cm$^3$/g, an average pore diameter of 80 A and a specific surface area of 375 m$^2$/g.

The catalyst layer is kept at 270° C. (injection chamber: 150° C.).

The hydrogen flow rate is 3.7 liters/hour (NTP) and 3-methylpiperidine is injected conjointly with an exactly measured flow rate of about 5.32 g/hour for one hour; the simultaneous injection is then continued with a hydrogen flow rate of 1 liter/hour (NTP) and an exactly measured 3-methylpiperidine flow rate of about 1.4 g/hour.

Table 6 collates the values of the DC, the Y and the productivity for two operating times.

TABLE 6

| Time in hours | DC % of the 3-methylpiperidine | Y % of β-picoline | Productivity in terms of β-picoline (g/hour/liter) |
|---|---|---|---|
| 1 | 67 | 100 | 3,350 |
| 3.5 | 75 | 100 | 1,000 |

A very rapid decrease in the productivity is observed.

We claim:

1. Process for preparation of compounds of the following general formula (I):

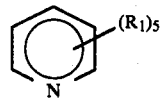

in which the radicals R$_1$, which are identical or different, represent a hydrogen atom or a linear or branched alkyl radical having 1 to 4 carbon atoms, by heating, in the vapor phase, at a temperature of 200° C. to 500° C.:
a compound of the following general formula (II):

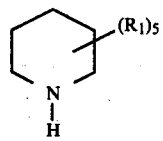

in which the radicals R$_1$ have the same meanings as above or
1,5-diaminopentane, or
1,5-diaminopentane containing, in its hydrocarbon part. from 1 to 3 linear or branched alkyl radicals having from 1 to 4 carbon atoms, or
a compound of the following general formula (III):

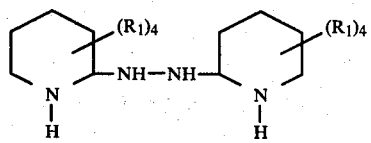

in which the radicals R$_1$ have the meanings indicated above, or
a mixture of several of the above compounds, the said process being characterized in that the reaction is carried out in the presence of a catalyst comprising palladium, platinum or ruthenium deposited on a macroporous solid support of which the average pore diameter is more than 200 Angstroms and of which the porous volume is between 0.5 and 1.4 cubic centimeters/gram.

2. Process according to claim 1, characterized in that the macroporous solid support is a silica, an alumina or carbon of which the average pore diameter is between 300 A and 5,000 A and of which the porous volume is between 0.8 and 1.2 cm$^3$/gram.

3. Process according to claim 1, characterized in that the metal used in the catalyst is palladium.

4. Process according to claim 2, characterized in that the metal used in the catalyst is palladium.

5. Process according to claim 1, characterized in that the catalyst used is palladium deposited on a silica of which the average pore diameter is between 300 A and 2,000 A and of which the porous volume is between 0.8 and 1.2 cm$^3$/g.

6. Process according to claim 2, characterized in that the catalyst used is palladium deposited on a silica of which the average pore diameter is between 300 A and 2,000 A and of which the porous volume is between 0.8 and 1.2 cm$^3$/g.

7. Process according to claim 1, characterized in that, in the catalyst, the weight ratio metal/macroporous solid support is less than or equal to 10%.

8. Process according to claim 2, characterized in that, in the catalyst, the weight ratio metal/macroporous solid support is less than or equal to 10%.

9. Process according to claim 5, characterized in that the weight ratio palladium/silica is between 0.2 and 2%.

10. Process according to claim 6, characterized in that the weight ratio palladium/silica is between 0.2 and 2%.

11. Process according to claim 1, characterized in that it is applied to:
piperidine;
piperidine of which the ring is substituted by one or more methyl or ethyl radicals;
1,5-diaminopentane;
1,5-diaminopentane of which the hydrocarbon part contains one or more methyl or ethyl substituents;
N,N'-bis-(piperidin-2-yl)-hydrazine;
N,N'-bis-(piperidin-2-yl)-hydrazine of which one piperidinyl ring or both the piperidinyl rings carry one or more methyl or ethyl radicals; and
mixtures of several of the above compounds.

12. Process according to claim 2, characterized in that it is applied to:
piperidine;
piperidine of which the ring is substituted by one or more methyl or ethyl radicals;
1,5-diaminopentane;
1,5-diaminopentane of which the hydrocarbon part contains one or more methyl or ethyl substituents;
N,N'-bis-(piperidin-2-yl)-hydrazine;
N,N'-bis-(piperidin-2-yl)-hydrazine of which one piperidinyl ring or both the piperidinyl rings carry one or more methyl or ethyl radicals; and
mixtures of several of the above compounds.

13. Process according to claim 1, characterized in that it is applied to: piperidine, 3-methylpiperidine, 5-ethyl-2-methylpiperidine, 1,5-diaminopentane, 2-methyl-1,5-diaminopentane, N,N'-bis-(piperidin-2-yl)-hydrazine, N,N'-bis-(3-methylpiperidin-2-yl)-hydrazine, N,N'-bis-(5-methylpiperidin-2-yl)-hydrazine, or N-(3-methylpiperidine-2-yl)-N'-(5-methylpiperidine-2-yl)-hydrazine or to mixtures of several of the above compounds.

14. Process according to claim 2, characterized in that it is applied to: piperidine, 3-methylpiperidine, 5-ethyl-2-methylpiperidine, 1,5-diaminopentane, 2-methyl-1,5-diaminopentane, N,N'-bis-(piperidin-2-yl)-hydrazine, N,N'-bis-(3-methylpiperidin-2-yl)-hydrazine, N,N'-bis-(5-methylpiperidin-2-yl)-hydrazine or N-(3-methylpiperidin-2-yl)-N'-(5-methylpiperidin-2-yl)-hydrazine, or to mixtures of several of the above compounds.

15. Process according to claim 1 characterized in that it is applied to the crude mixture obtained during the hydrogenation of 2-methylglutaronitrile.

16. Process according to claim 1, characterized in that the reaction is carried out at between 250° C. and 400° C.

17. Process according to claim 1, characterized in that the substrate or substrates to be treated and hydrogen are injected simultaneously.

18. Process according to claim 2, characterized in that it is applied to the crude mixture obtained during the hydrogenation of 2-methylglutaronitrile.

19. Process according to claim 2, characterized in that the reaction is carried out at between 250° C. and 400° C.

20. Process according to claim 2, characterized in that the substrate or substrates to be treated and hydrogen are injected simultaneously.

* * * * *